United States Patent
Shiratsuki et al.

(10) Patent No.: US 11,964,037 B2
(45) Date of Patent: Apr. 23, 2024

(54) HAIR-DYEING METHOD

(71) Applicant: KAO CORPORATION, Tokyo (JP)

(72) Inventors: Ko Shiratsuki, Sumida-ku (JP); Takahito Nakamura, Sumida-ku (JP)

(73) Assignee: KAO CORPORATION, Tokyo (JP)

(*) Notice: Subject to any disclaimer, the term of this patent is extended or adjusted under 35 U.S.C. 154(b) by 107 days.

(21) Appl. No.: 17/787,861

(22) PCT Filed: Dec. 14, 2020

(86) PCT No.: PCT/JP2020/046611
§ 371 (c)(1),
(2) Date: Jun. 21, 2022

(87) PCT Pub. No.: WO2021/131868
PCT Pub. Date: Jul. 1, 2021

(65) Prior Publication Data
US 2023/0048023 A1   Feb. 16, 2023

(30) Foreign Application Priority Data
Dec. 25, 2019 (JP) .................................. 2019-234954

(51) Int. Cl.
*A61Q 5/10* (2006.01)
*A61K 8/365* (2006.01)
*A61K 8/41* (2006.01)
*A61K 8/49* (2006.01)

(52) U.S. Cl.
CPC .............. *A61K 8/492* (2013.01); *A61K 8/365* (2013.01); *A61K 8/41* (2013.01); *A61Q 5/10* (2013.01); *A61K 2800/884* (2013.01)

(58) Field of Classification Search
CPC .......... A61K 8/492; A61K 8/365; A61K 8/41; A61K 2800/884; A61K 8/24; A61K 8/19; A61Q 5/10
USPC ........................................................... 8/407
See application file for complete search history.

(56) References Cited

U.S. PATENT DOCUMENTS

| | | | | |
|---|---|---|---|---|
| 5,665,336 A * | 9/1997 | Wolfram | .................. | A61Q 5/10 8/441 |
| 6,537,330 B1 * | 3/2003 | Hoeffkes | ................ | A61K 8/413 8/408 |
| 2010/0037404 A1 * | 2/2010 | Koike | ..................... | A61Q 5/10 8/423 |
| 2010/0125956 A1 * | 5/2010 | Koike | ..................... | A61K 8/39 8/429 |
| 2010/0154135 A1 * | 6/2010 | Matsunaga | .............. | A61Q 5/10 8/406 |
| 2010/0170048 A1 * | 7/2010 | Koike | .................... | A61K 8/676 8/406 |
| 2020/0360257 A1 | 11/2020 | Nagayama | | |

FOREIGN PATENT DOCUMENTS

| | | | | |
|---|---|---|---|---|
| JP | 6-40866 | A | 12/1994 | |
| JP | 2002-322039 | A | 11/2002 | |
| JP | 2007-326803 | A | 12/2007 | |
| JP | 2019-94328 | A | 6/2019 | |
| TH | 138524 | A * | 12/2014 | ............... A61Q 5/10 |
| TW | 201922219 | A | 6/2019 | |
| WO | WO 9966890 | A1 * | 12/1999 | ............. A61Q 5/065 |

OTHER PUBLICATIONS

International Search Report dated Feb. 22, 2021 in PCT/JP2020/046611 filed on Dec. 14, 2020, 2 pages.
Official communication issued on Dec. 22, 2023, in corresponding EP application No. 20904946.9.

* cited by examiner

*Primary Examiner* — Eisa B Elhilo
(74) *Attorney, Agent, or Firm* — Oblon, McClelland, Maier & Neustadt, L.L.P.

(57) ABSTRACT

A hair dyeing method that involves first step of applying on the hair a hair dye composition containing a compound represented by the following general formula (1A) or a salt thereof and an organic alkaline agent and having a pH of 9.0 or more and 11.0 or less:

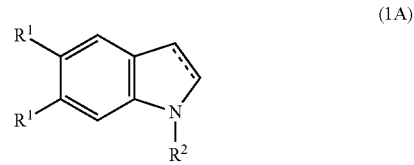

(1A)

wherein a broken line represents the presence or absence of a π bond; $R^1$ represents a hydroxy group or an acetoxy group; and $R^2$ represents a hydrogen atom, an acetyl group, a methyl group, or an ethyl group; and a second step of applying on the hair a hair treatment agent containing an organic acid or a salt thereof and having a pH of 5.5 or less. After performing the first step, the hair is subjected to the second step while maintaining in a wet state in which an amount of water per gram of the hair is 0.008 g or more.

6 Claims, No Drawings

HAIR-DYEING METHOD

CROSS-REFERENCE TO RELATED APPLICATIONS

The present application is a 35 U.S.C. § 371 national stage application of International patent application PCT/JP2020/046611, filed Dec. 14, 2020, which is based on and claims the benefit of priority to Japanese Application No. 2019-234954, filed Dec. 25, 2019. The entire contents of these applications are incorporated herein by reference.

FIELD OF THE INVENTION

The present invention relates to a hair dyeing method.

BACKGROUND OF THE INVENTION

There has hitherto been known an air oxidation type hair dye composition containing, as a coloring component for gray hair dyeing, 5,6-dihydroxyindole, 5,6-dihydroxyindoline, or a derivative thereof (these will be hereinafter generically named simply as a "dihydroxyindole derivative") that is a melanin precursor. Since an oxidizing agent is not used for such a melanin precursor, even in the case where the melanin precursor is used for a hair dye composition, hair damage is less and simplicity is high as a coloring component.

The hair dyed with the melanin precursor typically takes on a gray to black color. However, natural hair has a bright shade of color with a stronger reddish color as compared with the color dyed with the melanin precursor. Therefore, even when the melanin precursor is used as the coloring component, a demand for dyeing the hair to a more natural-looking shade of color is increasing.

For example, as a method for altering the color of hair dyed with a dihydroxyindole derivative to a natural-looking color without using a dihydroxyindole derivative or an additional masking coloring agent, PTL 1 (JP 6-040866 A) discloses a method including a step of treating dihydroxyindole-dyed hair with an acidic solution for an effective time and rinsing the treated hair.

SUMMARY OF THE INVENTION

The present invention relates to the following [1] to [2].
[1] A hair dyeing method including the following step 1 and step 2 in order, wherein after performing the step 1, hair is subjected to the step 2 while maintaining in a wet state in which an amount of water per gram of the hair is 0.008 g or more:
Step 1: a step of applying on the hair a hair dye composition (I) containing (A) a compound represented by the following general formula (1A) or a salt thereof and (B) an organic alkaline agent and having a pH of 9.0 or more and 11.0 or less:

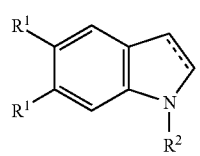

(1A)

wherein a broken line represents the presence or absence of a Π bond; $R^1$ represents a hydroxy group or an acetoxy group; and $R^2$ represents a hydrogen atom, an acetyl group, a methyl group, or an ethyl group; and
Step 2: a step of applying on the hair a hair treatment agent (II) containing (C) an organic acid or a salt thereof and having a pH of 5.5 or less.
[2] A hair dyeing kit provided with: a hair dye composition (I) containing (A) a compound represented or a salt thereof by the general formula (1A) and (B) an organic alkaline agent and having a pH of 9.0 or more and 11.0 or less and a hair treatment agent (II) containing (C) an organic acid or a salt thereof and having a pH of 5.5 or less.

DETAILED DESCRIPTION OF THE INVENTION

[Hair Dyeing Method]
A hair dyeing method of the present invention (hereinafter also referred to as a "hair dyeing method of the present invention" or simply as a "method of the present invention") is a method including the following step 1 and step 2 in order, wherein after performing the step 1, hair is subjected to the step 2 while maintaining in a wet state in which an amount of water per gram of the hair is 0.008 g or more:
Step 1: a step of applying on the hair a hair dye composition (I) containing (A) a compound represented by the following general formula (1A) or a salt thereof and (B) an organic alkaline agent and having a pH of 9.0 or more and 11.0 or less:

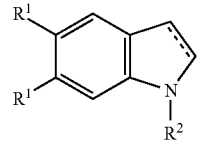

(1A)

wherein a broken line represents the presence or absence of a Π bond; $R^1$ represents a hydroxy group or an acetoxy group; and $R^2$ represents a hydrogen atom, an acetyl group, a methyl group, or an ethyl group; and
Step 2: a step of applying on the hair a hair treatment agent (II) containing (C) an organic acid or a salt thereof and having a pH of 5.5 or less.

In view of the fact that the present invention has the aforementioned constitution, it is possible to alter gray to black hair dyed with a hair dye composition containing the component (A) that is a melanin precursor in the step 1, to a bright shade of color with a stronger reddish color in a short time in the step 2.

In the method disclosed in the section of Examples in PTL 1, tresses are previously treated with a copper sulfate aqueous solution and then dyed with the dihydroxyindole derivative, and subsequently, theses tresses are post-treated with various acidic solutions, whereby a hair color having a shade of color that is warmer and redder than the color produced by the dihydroxyindole derivative and that is more natural-looking is obtained.

However, according to the method, in order to alter the hair to a desired hair color, it takes a time for the treatment with the acidic solution, and there is a concern that the scalp or hair is damaged. In addition, from the viewpoints that a degree of change in color tone is low and that the gray to black hair dyed with the dihydroxyindole derivative is altered to a bright shade of color with a reddish color, there is room for improvement. Furthermore, in view of the fact of using a heavy metal-containing catalyst, it is not a method that is said to be preferred from the viewpoint of environmental safety.

An object of the present invention is to provide a hair dyeing method for making it possible to dye gray to black hair dyed with a hair dye composition containing a melanin precursor, to a bright natural shade of color with a stronger reddish color.

The present inventors have found that in a hair dyeing method including a step 1 of applying on hair a hair dye composition containing a predetermined melanin precursor and a step 2 of applying on the hair a predetermined hair treatment agent in order, by regulating the pH of the hair dye composition to a relatively high pH value as 9.0 or more and 11.0 or less and using an organic alkaline agent as an alkaline agent, the hair can be dyed to a bright shade of color with a stronger reddish color after the hair treatment agent is applied in the step 2. Furthermore, the present inventors have found that after performing the step 1, by subjecting the hair to the step 2 while maintaining the hair in a predetermined wet state, the shade of color is altered in a shorter time, thereby making it possible to solve the problem.

According to the method of the present invention, it is possible to alter hair dyed with a melanin precursor, which typically takes on a gray to black color, to a bright natural shade of color with a stronger reddish color in a short time. Therefore, the hair treatment time can be made very short, and excellent simplicity in practical use is revealed.

<Step 1>

The step 1 is a step of applying on hair a hair dye composition (I) containing (A) a compound represented by the following general formula (1A) or a salt thereof and (B) an organic alkaline agent and having a pH of 9.0 or more and 11.0 or less. In the step 1, hair dyeing is performed by applying the hair dye composition (I) by, for example, coating or impregnating hair therewith.

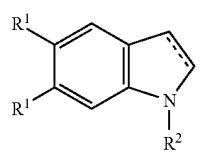

(1A)

In the formula, a broken line represents the presence or absence of a n bond; $R^1$ represents a hydroxy group or an acetoxy group; and $R^2$ represents a hydrogen atom, an acetyl group, a methyl group, or an ethyl group.

(Hair Dye Composition (I))

The hair dye composition (I) contains (A) a compound represented by the general formula (1A) or a salt thereof and (B) an organic alkaline agent and has a pH of 9.0 or more and 11.0 or less.

[(A) Compound Represented by General Formula (1A) or Salt Thereof]

The hair dye composition (I) contains a component (A) that is a compound represented by the following general formula (1A) or a salt thereof.

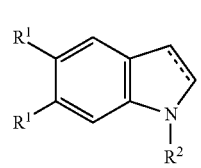

(1A)

In the formula, a broken line represents the presence or absence of a n bond; $R^1$ represents a hydroxy group or an acetoxy group; and $R^2$ represents a hydrogen atom, an acetyl group, a methyl group, or an ethyl group.

The melanin precursor of the component (A) is an indole derivative or indoline derivative that is the compound represented by the general formula (1A), or a salt thereof, and in the present invention, can be used alone or in combination of two or more thereof.

From the viewpoints of availability and hair dyeing properties of the component (A) and dyeing the hair to a bright shade of color with a strong reddish color, in the general formula (1), $R^1$ and $R^2$ are each preferably a hydrogen atom.

Examples of the compound represented by the general formula (1A) include 5,6-dihydroxyindole, N-methyl-5,6-dihydroxyindole, N-ethyl-5,6-dihydroxyindole, N-acetyl-5,6-dihydroxyindole, 5-acetoxy-6-hydroxyindole, 5,6-dihydroxyindoline, N-methyl-5,6-dihydroxyindoline, N-ethyl-5,6-dihydroxyindoline, N-acetyl-5,6-dihydroxyindoline, and 5-acetoxy-6-hydroxyindoline.

Examples of the salt of the compound represented by the general formula (1) include a hydrochloride, a hydrobromide, a sulfate, a phosphate, an acetate, a propionate, a lactate, and a citrate of the compound. Above all, a hydrobromide is preferred from the viewpoint of availability.

From the viewpoint of dyeing the hair to a natural shade of color, the component (A) is preferably one or more selected from the group consisting of 5,6-dihydroxyindole, 5,6-dihydroxyindoline, and salts thereof, more preferably 5,6-dihydroxyindole or a salt thereof, and still more preferably 5,6-dihydroxyindole.

From the viewpoint of obtaining high hair dyeing properties, the content of the component (A) in the hair dye composition (I) is preferably 0.05% by mass or more, more preferably 0.1% by mass or more, still more preferably 0.2% by mass or more, and yet still more preferably 0.3% by mass or more, and from the viewpoint of dyeing the hair to a bright shade of color with a strong reddish color and the viewpoint of economy, is preferably 5% by mass or less, more preferably 3% by mass or less, still more preferably 1% by mass or less, and yet still more preferably 0.8% by mass or less.

[(B) Organic Alkaline Agent]

The hair dye composition (I) contains an organic alkaline agent as a component (B). The component (B) has an action to improve the hair dyeing properties through an action of swelling the hair to open the cuticle and penetrating the coloring component, such as the component (A), into the interior of the hair. In addition, when hair dyeing is performed using the hair dye composition (I) containing the organic alkaline agent in the step 1, during the step 2, an alternation in shade of color of hair becomes large, and the hair can be dyed to a bright shade of color with a stronger reddish color.

As the component (B), an organic alkaline agent can be used without particular restrictions so long as it is typically used for hair dye compositions. Examples of the organic alkaline agent include: ammonia; alkanolamines, such as mono-, di-, or trimethanolamine, mono-, di-, or triethanolamine, trishydroxymethylaminomethane, and 2-amino-2-methyl-1-propanol; alkylamines, such as methylamine, dimethylamine, ethylamine, diethylamine, N-methylethylamine, propylamine, and butylamine; and aralkylamines, such as benzylamine. These can be used alone or in combination of two or more thereof. The number of carbon atoms of the alkanolamine, alkylamine, or aralkylamine is preferably 10 or less, and more preferably 8 or less from the viewpoint of water solubility.

Above all, from the viewpoint of dyeing the hair to a bright shade of color with a strong reddish color, the component (B) preferably contains one or more selected from the group consisting of ammonia, an alkanolamine, an alkylamine, and an aralkylamine, more preferably contains one or more of ammonia and an alkanolamine, and still more preferably contains an alkanolamine. From the viewpoint of dyeing the hair to a bright shade of color with a strong reddish color, in particular, the alkanolamine preferably contains one or more selected from the group consisting of monoethanolamine, trishydroxymethylaminomethane, and 2-amino-2-methyl-1-propanol, more preferably contains one or more selected from the group consisting of monoethanolamine and 2-amino-2-methyl-1-propanol, and still more preferably contains 2-amino-2-methyl-1-propanol.

From the viewpoint of dyeing the hair to a bright shade of color with a strong reddish color, the content of the alkanolamine in the component (B) is preferably 70% by mass or more, more preferably 80% by mass or more, and still more preferably 90% by mass or more, and preferably 100% by mass or less.

From the viewpoint of obtaining high hair dyeing properties and the viewpoint of dyeing the hair to a bright shade of color with a strong reddish color, the content of the component (B) in the hair dye composition (I) is preferably 0.1% by mass or more, more preferably 0.5% by mass or more, and still more preferably 1% by mass or more, and from the viewpoint of suppressing irritation, is preferably 10% by mass or less, more preferably 8% by mass or less, and still more preferably 5% by mass or less.

[Compound Represented by General Formula (1B) or Salt Thereof]

In the present invention, in the case of dyeing the hair to a bright shade of color with a stronger reddish color, the hair dye composition (I) can further contain, as a coloring component, a compound represented by the following general formula (1B) or a salt thereof.

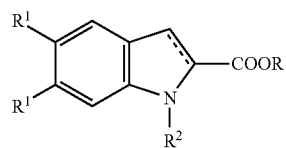

(1B)

In the formula, a broken line represents the presence or absence of Π bond; $R^1$ represents a hydroxy group or an acetoxy group; $R^2$ represents a hydrogen atom, an acetyl group, a methyl group, or an ethyl group; and R represents a hydrogen atom, a methyl group, or an ethyl group.

The compound represented by the general formula (1B) is an indole carboxylic acid derivative, an indoline carboxylic acid derivative, or a salt thereof, and in the present invention, can be used alone or in combination of two or more thereof. Above all, from the viewpoint of high hair dyeing properties, an indole carboxylic acid derivative or a salt thereof is preferred.

From the viewpoints of availability and hair dyeing properties of the compound represented by the general formula (1B) and dyeing the hair to a bright shade of color with a strong reddish color, in the general formula (1B), $R^1$ is preferably a hydroxy group, and $R^2$ is preferably a hydrogen atom.

Examples of the compound represented by the general formula (1B) include 5,6-dihydroxyindole-2-carboxylic acid, methyl 5,6-dihydroxyindole-2-carboxylate, ethyl 5,6-dihydroxyindole-2-carboxylate, N-methyl-5,6-dihydroxyindole-2-carboxylic acid, N-ethyl-5,6-dihydroxyindole-2-carboxylic acid, N-acetyl-5,6-dihydroxyindole-2-carboxylic acid, 5-acetoxy-6-hydroxyindole-2-carboxylic acid, 5,6-dihydroxyindoline-2-carboxylic acid, methyl 5,6-dihydroxyindoline-2-carboxylate, ethyl 5,6-dihydroxyindoline-2-carboxylate, N-methyl-5,6-dihydroxyindoline-2-carboxylic acid, N-ethyl-5,6-dihydroxyindoline-2-carboxylic acid, N-acetyl-5,6-dihydroxyindoline-2-carboxylic acid, and 5-acetoxy-6-hydroxyindoline-2-carboxylic acid.

Examples of the salt of the compound represented by the general formula (1B) include a hydrochloride, a hydrobromide, a sulfate, a phosphate, an acetate, a propionate, a lactate, and a citrate of the compound. Above all, a hydrobromide is preferred from the viewpoint of availability.

In the general formula (1B), when R is a hydrogen atom, examples of the salt of the compound represented by the general formula (1B) include carboxylates thereof (—COOR is —COO$^-$X$^+$ (X$^+$ is a cation, such as an alkali metal ion, e.g., Na$^+$ and K$^+$, an alkaline earth metal ion, e.g., Ca$^+$ and Mg$^+$, and an ammonium ion)).

From the viewpoint of dyeing the hair to a bright shade of color with a stronger reddish color, the compound represented by the general formula (1B) is preferably one or more selected from the group consisting of 5,6-dihydroxyindole-2-carboxylic acid, methyl 5,6-dihydroxyindole-2-carboxylate, ethyl 5,6-dihydroxyindole-2-carboxylate, and salts thereof, more preferably 5,6-dihydroxyindole-2-carboxylic acid or a salt thereof, and still more preferably 5,6-dihydroxyindole-2-carboxylic acid.

In the case of using the compound represented by the general formula (1B), from the viewpoint of dyeing the hair to a shade of color with a bright reddish color, the content of the compound represented by the general formula (1B) in the hair dye composition (I) is preferably 0.001% by mass or more, more preferably 0.005% by mass or more, still more preferably 0.01% by mass or more, yet still more preferably 0.05% by mass or more, and even yet still more preferably 0.08% by mass or more, and from the viewpoint of obtaining high hair dyeing properties and the viewpoint of economy, is preferably 2.5% by mass or less, more preferably 1.5% by mass or less, still more preferably 1% by mass or less, yet still more preferably 0.5% by mass or less, and even yet still more preferably 0.25% by mass or less.

From the viewpoint of obtaining high hair dyeing properties, a total content of the component (A) and the compound represented by the general formula (1B) in the hair dye composition (I) is preferably 0.06% by mass or more, more preferably 0.1% by mass or more, still more preferably 0.2% by mass or more, and yet still more preferably 0.3% by mass or more, and from the viewpoint of dyeing the hair to a bright shade of color with a strong reddish color and the view point of economy, is preferably 7.5% by mass or less, more preferably 5% by mass or less, still more preferably 3% by mass or less, and yet still more preferably 1% by mass or less.

[Other Component]

The hair dye composition (I) appropriately contains, in addition to the components, a component that is typically used for hair dye compositions within a range where the object of the present invention is not impaired. Examples of the component include a surfactant, a pH adjuster, a viscosity modifier, an antioxidant, silicone, an aromatic alcohol, a dyeing agent other than the component (A), a polymer, an oil, an anti-dandruff agent, a vitamin, a disinfectant, an antiinflammatory agent, an antiseptic, a chelating agent, a humectant, a pearlescent agent, a ceramide, a perfume, and an ultraviolet absorber.

According to the method of the present invention, in the hair dye composition (I), the hair can be dyed to a bright shade of color with a strong reddish color even when other coloring component than the component (A) and the compound represented by the general formula (1B) is not used. In consequence, the hair dye composition (I) may not substantially contain a coloring component other than the component (A) and the compound represented by the general formula (1B). The wording "not substantially contain" means that the content in the hair dye composition (I) is preferably 1% by mass or less, more preferably 0.5% by mass or less, still more preferably 0.2% by mass or less, and yet still more preferably 0% by mass.

Examples of the coloring component other than the component (A) and the compound represented by the general formula (1B) include an oxidation dye (constituted of a precursor and a coupler) and a direct dye, each of which is typically used for hair dye compositions.

[Aqueous Medium]

The hair dye composition (I) typically contains an aqueous medium. Examples of the aqueous medium include: water; a lower alcohol, such as ethanol and isopropyl alcohol; and a low-molecular diol or triol having 6 or less carbon atoms, such as 1,3-butylene glycol, glycerin, ethylene glycol, and propylene glycol, and from the viewpoint of affinity with the hair, one or more selected from the group consisting of water and ethanol are preferred.

The content of the aqueous medium in the hair dye composition (I) is typically within a range of 1% by mass to 99% by mass, and can be appropriately chosen according to a formulation thereof. From the viewpoint of easiness of rinsing the hair, the content of the aqueous medium in the hair dye composition (I) is preferably 50% by mass or more, more preferably 70% by mass or more, and still more preferably 80% by mass or more, and from the viewpoint of facilitating drying of the hair after the hair treatment, is preferably 98% by mass or less.

The formulation of the hair dye composition (I) is not particularly restricted, and it is possible to take any formulation, for example, a liquid, a foam, a paste, a cream, a solid, and a powder. From the viewpoint of applying the hair dye composition (I) on the hair through coating, impregnation, or the like, the formulation of the hair dye composition (I) is preferably a liquid, a paste, or a cream, and more preferably a liquid.

A method of producing the hair dye composition (I) is not particularly limited. For example, the hair dye composition (I) can be produced by blending the component (A), the component (B), the compound represented by the general formula (1B) as any component, and, if desired, other components to be used, and mixing them using a known stirring device or the like.

[pH]

From the viewpoint of improving the hair dyeing properties and the viewpoint of altering to a bright shade of color with a stronger reddish color in the step 2, the pH of the hair dye composition (I) is 9.0 or more, preferably more than 9.5, and more preferably 9.8 or more. In addition, from the viewpoint of obtaining high hair dyeing properties and the viewpoint of suppressing any damage against the hair, the pH is 11.0 or less, preferably 10.8 or less, and more preferably 10.5 or less.

The pH is a measured value at 25° C., and specifically, can be measured by a method described in the section of Examples.

In the step 1, the hair dye composition (I) is applied on the hair. A method for applying the hair dye composition (I) on the hair may be any method so long as it is possible to bring the hair dye composition (I) into contact with the hair. Examples thereof include a method for coating the hair in a dry state or wet state with the composition, and a method for impregnating the hair in a dry state or wet state with the composition.

From the viewpoint of a balance between hair dyeing properties and economy, the amount of the hair dye composition (I) to be applied on the hair is preferably 1/0.2 to 1/20, more preferably 1/0.5 to 1/10, and still more preferably 1/2 to 1/8 in terms of a bath ratio [(dry mass of hair)/(mass of hair dye composition)]. The dry mass of hair means a mass of hair when the hair is washed with a shampoo, dried by being blown with a hot air of a dryer for 30 minutes, and then allowed to stand for a whole day and night or longer at a temperature of 25° C. and a relative humidity of 65%.

The hair that is an object of the application is preferably hair of head and may be at least a part of the hair of head.

In the case of coating the hair with the hair dye composition (I), from the viewpoint of penetrating the component (A) into the hair, a coating time is preferably 10 seconds or longer, and more preferably 20 seconds or longer, and from the viewpoint of reducing a burden on the operator, is preferably 10 minutes or shorter, and more preferably 5 minutes or shorter. In addition, in the case of impregnating the hair with the hair dye composition (I), from the viewpoint of penetrating the component (A) into the hair, an impregnation time is preferably 1 minute or longer, and more preferably 3 minutes or longer, and from the viewpoint of reducing a burden on the operator, is preferably 60 minutes or shorter, and more preferably 30 minutes or shorter.

After coating or impregnating the hair with the hair dye composition (I), it is preferred to perform a step of further allowing the resulting hair to stand. From the viewpoint of penetrating the component (A) into the hair, a standing time on this occasion is preferably 1 minute or longer, and more preferably 3 minutes or longer, and from the viewpoint of reducing a burden on the operator, is preferably 30 minutes or shorter, and more preferably 20 minutes or shorter.

In the step 1, though it is possible to appropriately vary a time for applying the hair dye composition (I) on the hair, namely a total of the time of coating or impregnating the hair with the hair dye composition (I) and the standing time, it is preferably 30 seconds or longer, more preferably 2 minutes or longer, and still more preferably 4 minutes or longer from the viewpoint of penetrating the component (A) into the hair, and it is preferably 90 minutes or shorter, more preferably 60 minutes or shorter, still more preferably 50 minutes or shorter, and yet still more preferably 40 minutes or shorter from the viewpoint of reducing a burden on the operator.

Although a temperature during the step 1 is not particularly restricted, it is preferably 40° C. or lower, and more preferably 35° C. or lower from the viewpoint of handleability of the hair dye composition (I). In addition, it is preferably 25° C. or higher, and more preferably 30° C. or higher from the viewpoint of improving the hair dyeing properties.

<Rinsing Step>

From the viewpoint of removing the component (A) which has not been penetrated into the hair, it is preferred that the method of the present invention includes a step of rinsing the hair (hereinafter also referred to simply as a "rinsing step") between the step 1 and the step 2. The rinsing step is, for example, performed by washing away, with water, the hair dye composition (I) having been applied on the hair.

<Drying Step>

The method of the present invention can appropriately include a step of drying the hair (hereinafter also referred to simply as a "drying step") between the step 1 and the step 2. However, from the viewpoints that the hair is dyed to a bright shade of color with a strong reddish color and that in the step 2 as mentioned later, after coating or impregnating the hair with the hair treatment agent (II), the standing time in the case of performing the standing step is shortened, after the performing the step 1, the hair is subjected to the step 2 while maintaining in a wet state in which the amount of water per gram of the hair is 0.008 g or more.

The step of drying the hair is a step of reducing the amount of water of the hair, and in order to positively reduce water of the hair, examples thereof include towel drying, drying with a dryer (cool air or hot air), air-drying, and a combination of two or more of these drying treatments.

Specifically, from the viewpoint of dyeing the hair to a shade of color with a strong reddish color, as for the wet state of hair, the amount of water per gram of the hair to be subjected to the step 2 after performing the step 1 is set to preferably 0.01 g or more, more preferably 0.05 g or more, still more preferably 0.1 g or more, yet still more preferably 0.2 g or more, even yet still more preferably 0.5 g or more, and even still more preferably 0.8 g or more. Although an upper limit value of the amount of water per gram of the hair to be subjected to the step 2 after performing the step 1 is not particularly restricted, it is typically 5 g or less, and from the viewpoint of suppressing water dripping from the hair and improving the operability, it is set to preferably 3 g or less, more preferably 2 g or less, and still more preferably 1.2 g or less.

In the case of performing towel drying or the like as the drying step between the step 1 and the step 2, it is preferred to keep the amount of water per gram of the hair to the aforementioned range after performing the step 1 but before subjecting the hair to the step 2.

Specifically, the amount of water per gram of the hair can be determined by a method described in the section of Examples.

<Step 2>

The step 2 is a step of applying on the hair the hair treatment agent (II) containing (C) an organic acid or a salt thereof and having a pH of 5.5 or less. In the step 2, by applying the hair treatment agent (II) on the hair, color shift of the coloring component penetrated into the hair is generated, whereby it is possible to dye the hair to a bright shade of color with a strong reddish color.

(Hair Treatment Agent (II))

The hair treatment agent (II) contains (C) the organic acid or salt thereof and has a pH or 5.5 or less.

[(C) Organic Acid or Salt Thereof]

The hair treatment agent (II) contains an organic acid or a salt thereof as a component (C). The component (C) is preferably one or more selected from the group consisting of an aliphatic carboxylic acid having 8 or less carbon atoms, an aromatic sulfonic acid having 10 or less carbon atoms, and salts thereof from the viewpoint of dyeing the hair to a bright shade of color with a strong reddish color, the viewpoint of solubility in the hair treatment agent (II), and the viewpoint of suppressing any damage against the scalp or hair. In this specification, the "aliphatic carboxylic acid" means a carboxylic acid containing neither an aromatic ring nor a heterocyclic ring. In addition, the aliphatic carboxylic acid may have a hydroxy group.

As the component (C), a salt of an organic acid can also be used. Examples of the salt include: an ammonium salt, such as an ammonium salt, and an alkyl ammonium salt; an alkali metal salt, such as a sodium salt and a potassium salt; and an alkaline earth metal salt, such as a calcium salt and a magnesium salt, with an ammonium salt, a sodium salt, or a potassium salt being preferred.

Examples of the aliphatic carboxylic acid having 8 or less carbon atoms or a salt thereof include malic acid, citric acid, lactic acid, glycolic acid, malonic acid, maleic acid, glyceric acid, tartaric acid, and salts thereof. Above all, one or more selected from the group consisting of malic acid, citric acid, lactic acid, glycolic acid, glyceric acid, tartaric acid, and salts thereof are preferred.

Examples of the aromatic sulfonic acid having 10 or less carbon atoms or a salt thereof include benzenesulfonic acid, p-toluenesulfonic acid, 2,4-dimethylbenzenesulfonic acid, 2,5-dimethylbenzenesulfonic acid, naphthalenesulfonic acid, saccharin, and salts thereof. Above all, one or more selected from the group consisting of p-toluenesulfonic acid, naphthalenesulfonic acid, and salts thereof are preferred.

The component (C) can be used alone or in combination of two or more thereof.

Above all, from the viewpoint of dyeing the hair to a bright shade of color with a strong reddish color, the viewpoint of solubility in the hair treatment agent (II), and the viewpoint of suppressing any damage against the scalp or hair, the component (C) preferably contains an aliphatic carboxylic acid having 8 or less carbon atoms or a salt thereof, more preferably contains one or more selected from the group consisting of malic acid, citric acid, lactic acid, glycolic acid, glyceric acid, tartaric acid, and salts thereof, and still more preferably contains lactic acid or a salt thereof.

From the viewpoint of dyeing the hair to a bright shade of color with a strong reddish color, the viewpoint of solubility in the hair treatment agent (II), and the viewpoint of suppressing any damage against the scalp or hair, the content of the aliphatic carboxylic acid having 8 or less carbon atoms or a salt thereof in the component (C) is preferably 70% by mass or more, more preferably 80% by mass or more, and still more preferably 90% by mass or more, and preferably 100% by mass or less.

From the viewpoint of dyeing the hair to a bright shade of color with a strong reddish color, the content of the component (C) in the hair treatment agent (II) is preferably 1% by mass or more, more preferably 3% by mass or more, and still more preferably 5% by mass or more, and from the viewpoint of suppressing any damage against the scalp or hair, it is preferably 30% by mass or less, more preferably 20% by mass or less, and still more preferably 15% by mass or less. In the case where the component (C) is an organic acid salt, the content of the component (C) in the hair treatment agent (II) means the content as expressed in terms of an organic acid.

[Other Component]

The hair treatment agent (II) may appropriately contain a component other than the aforementioned components within a range where the object of the present invention is not impaired. Examples of the component include the components exemplified as the "other component" in the hair dye composition (I), and for example, a pH adjuster or a viscosity modifier can be contained.

[Aqueous Medium]

The hair treatment agent (II) typically contains an aqueous medium. Examples of the aqueous medium include the components exemplified in the hair dye composition (I), and water is preferred from the viewpoint of affinity with the hair.

Although the content of the aqueous medium in the hair treatment agent (II) can be appropriately chosen according to a formulation thereof, it is typically in range of 1% by mass to 99% by mass. From the viewpoint of easiness of rinsing the hair, the content of the aqueous medium in the hair treatment agent (II) is preferably 50% by mass or more, more preferably 70% by mass or more, and still more preferably 80% by mass or more, and from the viewpoint of facilitating drying of the hair after the hair treatment, is preferably 98% by mass or less.

The formulation of the hair treatment agent (II) is not particularly restricted, and it is possible to take any formulation, for example, a liquid, a foam, a paste, and a cream. From the viewpoint of applying the hair treatment agent (II) on the hair through coating, impregnation, or the like, the formulation of the hair treatment agent (II) is preferably a liquid, a paste, or a cream, and more preferably a liquid.

A method of producing the hair treatment agent (II) is not particularly limited, and for example, the hair treatment agent (II) can be produced by blending the component (C) and, if desired, other components to be used, and mixing them using a known stirring device or the like.

[pH]

From the viewpoint of dyeing the hair to a bright shade of color with a strong reddish color, the pH of the hair treatment agent (II) is 5.5 or less, preferably 4.5 or less, still more preferably 4.0 or less, yet still more preferably less than 4.0, and even yet still more preferably 3.8 or less. In addition, from the viewpoint of obtaining high hair dyeing properties and the viewpoint of suppressing any damage against the scalp or hair, the pH is preferably 2.0 or more, and more preferably 2.3 or more.

The pH is a measured value at 25° C., and specifically, can be measured by a method described in the section of Examples.

In the step 2, the hair treatment agent (II) is applied on the hair. A method for applying the hair treatment agent (II) on the hair may be any method so long as it is possible to bring the treatment agent into contact with the hair, and examples thereof include a method for coating the hair with the treatment agent, and a method for impregnating the hair with the treatment agent.

From the viewpoint of dyeing the hair to a bright shade of color with a strong reddish color, the amount of the hair treatment agent (II) to be applied on the hair is preferably 1/0.2 to 1/20, more preferably 1/0.5 to 1/10, and still more preferably 1/0.5 to 1/5 in terms of a bath ratio [(dry mass of hair)/(mass of hair treatment agent)].

A time for coating or impregnating the hair with the hair treatment agent (II) is not particularly restricted so long as it is possible to thoroughly apply the hair treatment agent (II) on the hair, and the time can be varied according to the amount of hair to be applied, the shape of hair, or the like.

In order to dye the hair to a bright shade of color with a stronger reddish color, after coating or impregnating the hair with the hair treatment agent (II), a step of standing can be further performed. In the present invention, even if the step of standing is not included, the hair can be dyed to a bright shade of color with a thoroughly strong reddish color, and from the viewpoint of dyeing the hair to a bright shade of color with a further stronger reddish color, a standing time on this occasion can be set to preferably 30 seconds or longer, more preferably 1 minute or longer, and still more preferably 2 minutes or longer. In addition, from the viewpoints of reducing a burden on the operator and suppressing any damage against the scalp or hair, the standing time can be set to preferably shorter than 10 minutes, more preferably 5 minutes or shorter, and still more preferably 3 minutes or shorter.

In the case where the hair has been impregnated with the hair treatment agent (II), the hair can be allowed to stand in a state in which it is impregnated with the hair treatment agent, or the step of standing can be performed after lifting up the hair from the hair treatment agent.

In the step 2, though it is possible to appropriately vary a time for applying the hair treatment agent (II) on the hair, namely a total of the time of coating or impregnating the hair with the hair treatment agent (II) and the standing time, it is preferably 10 seconds or longer, and more preferably 20 seconds or longer from the viewpoint of dyeing the hair to a bright shade of color with a strong reddish color, and it is preferably 10 minutes or shorter, more preferably 6 minutes or shorter, and still more preferably 4 minutes or shorter from the viewpoints of reducing a burden on the operator and suppressing any damage against the scalp or hair.

Although a temperature during the step 2 is not particularly restricted, it is preferably 40° C. or lower, and more preferably 35° C. or lower from the viewpoint of handleability of the hair treatment agent (II). In addition, it is preferably 25° C. or higher, and more preferably 30° C. or higher from the viewpoint of improving the hair dyeing properties.

In the step 2, after applying the hair treatment agent (II) on the hair, and preferably after allowing the resulting hair to stand, it is preferred to perform a step of rinsing the hair (rinsing step). The rinsing step is, for example, performed by washing away, with water, the hair treatment agent (II) having been applied on the hair.

After performing the rinsing step, a step of drying the hair may be performed. Also, the hair may be again subjected to the step 1 without performing the step of drying the hair.

The method of the present invention includes the aforementioned step 1 and step 2 in order, and after performing the step 1, the hair may be subjected to the step 2 while maintaining in a wet state in which the amount of water per gram of the hair is 0.008 g or more, and the number of times for performing each of the steps is not particularly restricted. For example, in the method of the present invention, the step 1 and the step 2 may be successively performed one at a time; after repeatedly performing the step 1 two or more times, the step 2 may be performed; or after performing the step 1, the step 2 may be repeatedly two or more times. Furthermore, such a cycle may be repeatedly performed. From the viewpoint of dyeing the hair to a bright shade of color with a stronger reddish color, it is preferred to successively perform the step 1 and the step 2 one at a time, and this cycle may be repeated until a desired dyed hair color is obtained.

From the viewpoint of dyeing the hair to a bright shade of color with a strong reddish color and the viewpoint of environmental safety, it is preferred that the method of the present invention does not substantially include a step of applying a metal-based oxidation catalyst on the hair. The metal-based oxidation catalyst as referred to herein is a compound not only containing a metal but also having an action to promote oxidation of the component (A), and specifically, examples thereof include one or more metal or transition metal selected from the group consisting of iron, cobalt, manganese, copper, silver, titanium, zirconium, tantalum, chromium, nickel, palladium, platinum, gold, mercury, cadmium, zinc, tin, antimony, lead, and bismuth. More specifically, examples thereof include one or more selected from the group consisting of copper sulfate, nickel chloride, ferric sulfate, lead acetate, manganese sulfate, and zinc nitrate. In addition, the wording "applying the metal-based oxidation catalyst on the hair" means that the metal-based oxidation catalyst or a solution thereof is brought into contact with the hair before dyeing or after dyeing through coating, impregnation, or the like. The wording "not substantially including the step of applying the metal-based oxidation catalyst on the hair" means that a step of applying a composition containing 0.01% by mass or more of the metal-based oxidation catalyst on the hair is not included.

When the metal-based oxidation catalyst is applied on the hair, oxidation of the component (A) in the hair dye composition (I) having been applied on the hair in the step 1 excessively proceeds, whereby a phenolic hydroxy group in the component (A) or an oxide thereof is oxidized to ketones. Therefore, it may be considered that even when the resultant is then subjected to the step 2, there is no room where a primary structure of the component (A) or an oxide thereof converts, so that the color shift to a reddish shade of color is hardly caused.

[Hair Dyeing Kit]

The present invention also provides a hair dyeing kit provided with a hair dye composition (I) containing (A) a compound represented by the following general formula (1A) or a salt thereof and (B) an organic alkaline agent and having a pH of 9.0 or more and 11.0 or less and a hair treatment agent (II) containing (C) an organic acid or a salt thereof and having a pH of 5.5 or less:

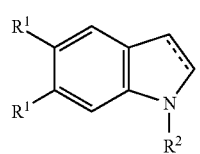

(1A)

wherein a broken line represents the presence or absence of a Π bond; $R^1$ represents a hydroxy group or an acetoxy group; and $R^2$ represents a hydrogen atom, an acetyl group, a methyl group, or an ethyl group.

The hair dye composition (I), the hair treatment agent (II), and preferred embodiments thereof are the same as those mentioned above.

The hair dyeing kit of the present invention may be provided with the hair dye composition (I) and the hair treatment agent (II), and examples thereof include a two-part type kit provided with the hair dye composition (I) and the hair treatment agent (II), each of which is enclosed in an individual container. The shape of the container is not particularly restricted but can be appropriately chosen according to the formulation thereof. Examples thereof include a bottle, a tube, a dispenser, and an aerosol.

The hair dyeing kit may be further provided with a comb, a brush, or the like, if desired, for the purpose of coating the hair with the hair dye composition (I) and the hair treatment agent (II).

Preferably, the hair dyeing kit of the present invention can be used according to the method described above for the hair dyeing method.

Regarding the aforementioned embodiments, the present invention discloses hair dyeing methods and hair dyeing kits.

<1> A hair dyeing method including the following step 1 and step 2 in order, wherein after performing the step 1, hair is subjected to the step 2 while maintaining in a wet state in which an amount of water per gram of the hair is 0.008 g or more:

Step 1: a step of applying on the hair a hair dye composition (I) containing (A) a compound represented by the following general formula (1A) or a salt thereof and (B) an organic alkaline agent and having a pH of 9.0 or more and 11.0 or less:

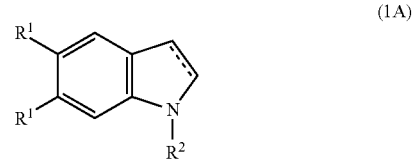

(1A)

wherein a broken line represents the presence or absence of a Π bond; $R^1$ represents a hydroxy group or an acetoxy group; and $R^2$ represents a hydrogen atom, an acetyl group, a methyl group, or an ethyl group; and Step 2: a step of applying on the hair a hair treatment agent (II) containing (C) an organic acid or a salt thereof and having a pH of 5.5 or less.

<2> A hair dyeing method including the following step 1 and step 2 in order and including a step of rinsing hair between the step 1 and the step 2, wherein after performing the step 1, the hair is subjected to the step 2 while maintaining in a wet state in which an amount of water per gram of the hair is 0.05 g or more and 2 g or less:

Step 1: a step of applying on the hair a hair dye composition (I) containing (A) 0.1% by mass or more and 3% by mass or less of a compound represented by the following general formula (1A) or a salt thereof and (B) 0.5% by mass or more and 8% by mass or less of an organic alkaline agent and having a pH of more than 9.5 and 11.0 or less, and standing for 1 minute or longer and 30 minutes or shorter:

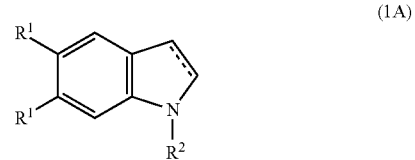

(1A)

wherein a broken line represents the presence or absence of a Π bond; $R^1$ represents a hydroxy group or an acetoxy group; and R² represents a hydrogen atom, an acetyl group, a methyl group, or an ethyl group; and Step 2: a step of applying on the hair a hair treatment agent (II) containing (C) 1% by mass or more and 30% by mass or less of an organic acid or a salt thereof and having a pH of 2.0 or more and 4.0 or less for 10 seconds or longer and 6 minutes or shorter.

<3> A hair dyeing method including the following step 1 and step 2 in order and including a step of rinsing hair between the step 1 and the step 2, wherein after performing the step 1, the hair is subjected to the step 2 while maintaining in a wet state in which an amount of water per gram of the hair is 0.2 g or more and 1.2 g or less:

Step 1: a step of applying on the hair a hair dye composition (I) containing (A) 0.2% by mass or more and 1% by mass or less of a compound represented by the following general formula (1A) or a salt thereof and (B) 1% by mass or more and 5% by mass or less of an organic alkaline agent and having a pH of 9.8 or more and 10.5 or less, and standing for 3 minutes or longer and 20 minutes or shorter:

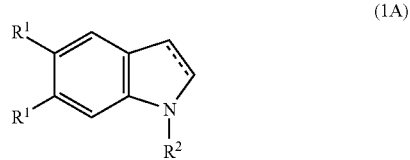
(1A)

wherein a broken line represents the presence or absence of a Π bond; R¹ represents a hydroxy group or an acetoxy group; and R² represents a hydrogen atom, an acetyl group, a methyl group, or an ethyl group; and Step 2: a step of applying on the hair a hair treatment agent (II) containing (C) 5% by mass or more and 15% by mass or less of an organic acid or a salt thereof and having a pH of 2.3 or more and 3.8 or less for 20 seconds or longer and 4 minutes or shorter.

<4> A hair dyeing kit provided with: a hair dye composition (I) containing (A) a compound represented by the following general formula (1A) or a salt thereof and (B) an organic alkaline agent and having a pH of 9.0 or more and 11.0 or less; and a hair treatment agent (II) containing (C) an organic acid or a salt thereof and having a pH of 5.5 or less:

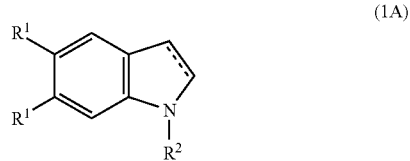
(1A)

wherein a broken line represents the presence or absence of a Π bond; R¹ represents a hydroxy group or an acetoxy group; and R² represents a hydrogen atom, an acetyl group, a methyl group, or an ethyl group.

<5> A hair dyeing kit provided with: a hair dye composition (I) containing (A) 0.1% by mass or more and 3% by mass or less of a compound represented by the following general formula (1A) or a salt thereof and (B) 0.5% by mass or more and 8% by mass or less of an organic alkaline agent and having a pH of more than 9.5 or 11.0 or less; and a hair treatment agent (II) containing (C) 1% by mass or more and 30% by mass or less of an organic acid or a salt thereof and having a pH of 2.0 or more and 4.0 or less:

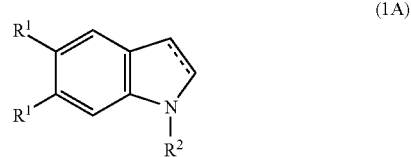
(1A)

wherein a broken line represents the presence or absence of a Π bond; R¹ represents a hydroxy group or an acetoxy group; and R² represents a hydrogen atom, an acetyl group, a methyl group, or an ethyl group.

<6> A hair dyeing kit provided with: a hair dye composition (I) containing (A) 0.2% by mass or more and 1% by mass or less of a compound represented by the following general formula (1A) or a salt thereof and (B) 1% by mass or more and 5% by mass or less of an organic alkaline agent and having a pH of 9.8 or more and 10.5 or less; and a hair treatment agent (II) containing (C) 5% by mass or more and 15% by mass or less of an organic acid or a salt thereof and having a pH of 2.3 or more and 3.8 or less:

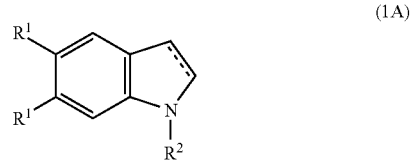
(1A)

wherein a broken line represents the presence or absence of a Π bond; R¹ represents a hydroxy group or an acetoxy group; and R² represents a hydrogen atom, an acetyl group, a methyl group, or an ethyl group.

<7> The hair dyeing method as set forth in any one of <1> to <3> or the hair dyeing kit as set forth in any one of <4> to <6>, wherein the component (A) contains one or more selected from the group consisting of 5,6-dihydroxyindole, 5,6-dihydroxyindoline, and salts thereof.

<8> The hair dyeing method as set forth in any one of <1> to <3> or the hair dyeing kit as set forth in any one of <4> to <6>, wherein the component (A) contains 5,6-dihydroxyindole or a salt thereof.

<9> The hair dyeing method as set forth in any one of <1> to <3> or the hair dyeing kit as set forth in any one of <4> to <6>, wherein the component (A) contains 5,6-dihydroxyindole.

<10> The hair dyeing method as set forth in any one of <1> to <3> or the hair dyeing kit as set forth in any one of <4> to <6>, wherein the component (B) contains one or more of ammonia and an alkanolamine.

<11> The hair dyeing method as set forth in any one of <1> to <3> or the hair dyeing kit as set forth in any one of <4> to <6>, wherein the component (B) contains one or more selected from the group consisting of monoethanolamine, trishydroxymethylaminomethane, and 2-amino-2-methyl-1-propanol.

<12> The hair dyeing method as set forth in any one of <1> to <3> or the hair dyeing kit as set forth in any one of <4> to <6>, wherein the component (B) contains one or more selected from the group consisting of monoethanolamine and 2-amino-2-methyl-1-propanol.

<13> The hair dyeing method as set forth in any one of <1> to <3> or the hair dyeing kit as set forth in any one of <4> to <6>, wherein the component (B) contains 2-amino-2-methyl-1-propanol.
<14> The hair dyeing method as set forth in any one of <1> to <3> or the hair dyeing kit as set forth in any one of <4> to <6>, wherein the component (C) contains one or more selected from the group consisting of an aliphatic carboxylic acid having 8 or less carbon atoms, an aromatic sulfonic acid having 10 or less carbon atoms, and salts thereof.
<15> The hair dyeing method as set forth in any one of <1> to <3> or the hair dyeing kit as set forth in any one of <4> to <6>, wherein the component (C) contains an aliphatic carboxylic acid having 8 or less carbon atoms or a salt thereof.
<16> The hair dyeing method as set forth in any one of <1> to <3> or the hair dyeing kit as set forth in any one of <4> to <6>, wherein the component (C) contains one or more selected from the group consisting of malic acid, citric acid, lactic acid, glycolic acid, glyceric acid, tartaric acid, and salts thereof.
<17> The hair dyeing method as set forth in any one of <1> to <3> or the hair dyeing kit as set forth in any one of <4> to <6>, wherein the component (C) contains lactic acid or a salt thereof.
<18> The hair dyeing method as set forth in any one of <1> to <3>, wherein after performing the step 1, the hair is subjected to the step 2 while maintaining in a wet state in which the amount of water per gram of the hair is 0.5 g or more and 1.2 g or less.
<19> The hair dyeing method as set forth in any one of <1> to <3>, wherein after performing the step 1, the hair is subjected to the step 2 while maintaining in a wet state in which the amount of water per gram of the hair is 0.8 g or more and 1.2 g or less.
<20> The hair dyeing method as set forth in any one of <1> to <3> or the hair dyeing kit as set forth in any one of <4> to <6>, wherein the hair dye composition (I) further contains a compound represented by the following general formula (1B) or a salt thereof:

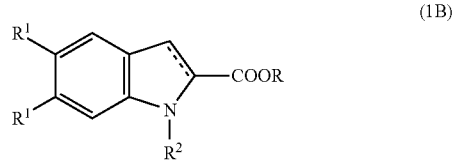

wherein a broken line represents the presence or absence of a Π bond; $R^1$ represents a hydroxy group or an acetoxy group; $R^2$ represents a hydrogen atom, an acetyl group, a methyl group, or an ethyl group; and R represents a hydrogen atom, a methyl group, or an ethyl group.
<21> The hair dyeing method as set forth in any one of <1> to <3>, not substantially including a step of applying a metal-based oxidation catalyst on the hair.
<22> The hair dyeing kit as set forth in any one of <4> to <6>, not containing a composition containing 0.01% by mass or more of a metal-based oxidation catalyst.

EXAMPLES

The present invention is hereunder described by reference to Examples, but it should be construed that the present invention is not limited to the scope of the Examples. In the present Examples, the preparation of tress for evaluation, the pH measurement, the measurement of the amount of water of hair, and the hair dyeing property evaluation were performed by the following methods.

[Preparation of Tress for Evaluation]

An untreated tress (gray hair tress of a Chinese woman having a length of 10 cm and a mass of 1 g (BM-W-A, manufactured by Beaulax Co., Ltd.)) was washed twice with a plain shampoo having the following composition, dried by being blown with a hot air of a dryer for 30 minutes, and then allowed to stand for a whole day and night or longer at a temperature of 25° C. and a relative humidity of 65% (hereinafter also referred to as "dry tress"). The mass of the tress at this time was taken as a dry mass.

| (Plain Shampoo) | (% by mass) |
|---|---|
| Sodium polyoxyethylene lauryl ether sulfate (EMAL E-27C (active component amount: 27% by mass), manufactured by Kao Corporation) | 57.4 |
| Lauramide DEA (AMINON L-02, manufactured by Kao Corporation | 1.5 |
| EDTA-2Na (FROST DS, manufactured by Daiichi Pure Chemical Co., Ltd.) | 0.3 |
| Phosphoric acid (adjusted to a pH of 7.0) | 0.5 |
| Sodium benzoate | |
| Purified water | Balance |
| Total | 100 |

[pH Measurement]

The pH of the hair dye composition and the hair treatment agent at 25° C. was measured with a pH meter (F-51, manufactured by HORIBA, Ltd.).

[Measurement of Amount of Water of Hair]

As for the amount of water of the tress in the hair treatment step, the mass of the tress in each of the treatment steps was measured, a difference from the mass of the dry tress was taken as the amount of water of the hair.

[Hair Dyeing Property evaluation]

A hue (a*) of the tress after the following treatment was measured at 6 points per tress by using a color color-difference meter (CR-400, manufactured by Konica Minolta, Inc.), and an average value thereof was calculated. The evaluation results are shown Tables 4 to 8. It is evaluated that as the value of a* is large, the hair is dyed to a shade of color with a reddish color, and the effects of the present invention are obtained.

Next, the hair dye compositions, the hair treatment agents, and the metal solutions used in the present invention were obtained by the following preparation methods.

Production Examples 1 to 4 (Preparation of Hair Dye Compositions A and B, Comparative C, and Comparative D)

The respective components were blended and mixed according to the composition shown in Table 1, thereby preparing the hair dye compositions A and B, comparative C, and comparative D. The blending amounts described in Table 1 are all described in terms of "% by mass" of the active component.

The prepared hair dye composition was kept in a nitrogen atmosphere and dispersed on each occasion of use, and then subjected to the hair dyeing property evaluation as mentioned later.

TABLE 1

| Hair dye composition | | Production Example 1<br>A | Production Example 2<br>B | Production Example 3 Comparative<br>C | Production Example 4 Comparative<br>D |
|---|---|---|---|---|---|
| Blending (% by mass) | (A1) 5,6-dihydroxyindole *1 | 0.5 | 0.5 | 0.5 | 0.5 |
| | (B1) Monoethanolamine | 3 | | | |
| | (B2) 2-amino-2-methyl-1-propanol | | 3 | | |
| | (b1) Sodium hydroxide | | | 3 | |
| | Ethanol | 10 | 10 | 10 | 10 |
| | Phosphoric acid | Moderate | Moderate | Moderate | 0 |
| | Purified water | Balance | Balance | Balance | Balance |
| pH | | 10.2 | 10.2 | 10.2 | 7 |

*1: A 5,6-dihydroxyindole solution (manufactured by Matrix Scientific, 5,6-dihydroxyindole: 1% by mass, ethanol: 20% by mass, water: balance) is blended so as to have the active components described in the table.

Production Examples 5 to 8 (Preparation of Hair Treatment Agents A to D)

The respective components were blended and mixed according to the composition shown in Table 2, thereby preparing the hair treatment agents A to D. The blending amounts described in Table 2 are all described in terms of "% by mass" of the active component.

TABLE 2

| Hair treatment agent | | Production Example 5<br>A | Production Example 6<br>B | Production Example 7<br>C | Production Example 8<br>D |
|---|---|---|---|---|---|
| Blending (% by mass) | (D1) Lactic acid *2 | 10 | 10 | 10 | 10 |
| | Sodium hydroxide | Moderate | Moderate | Moderate | Moderate |
| | Purified water | Balance | Balance | Balance | Balance |
| pH | | 2.5 | 3.0 | 3.5 | 4.0 |

*2: Manufactured by Musashino Chemical Laboratory, Ltd., a trade name "Musashino Lactic Acid 90"

Production Example 9 (Preparation of Metal Solution a)

The respective components were blended according to the composition shown in Table 3, thereby preparing the metal solution a. The blending amounts described in Table 3 are all described in terms of "% by mass" of the active component.

TABLE 3

| | | Production Example 9 |
|---|---|---|
| Metal solution | | a |
| Blending (% by mass) | Copper (II) sulfate | 1 |
| | Purified water | 99 |
| pH | | 7.0 |

Examples 1 and 2 and Comparative Example 1 (Examination Regarding Kind of Alkaline Agent in Hair Dye Composition (I))

(Step 1 and Rinsing Step)

The dry tress was impregnated with 5 g of the hair dye composition A or B or comparative C for 10 minutes in a nitrogen atmosphere (the bath ratio ((dry tress)/(hair dye composition)) during impregnation: 1/5).

Subsequently, the tress was lifted up from the hair dye composition and controlled by lightly squeezing such that the bath ratio ((dry tress)/(hair dye composition)) during standing was 1/1, followed by allowing to stand for 10 minutes in an air atmosphere. After a lapse of 10 minutes, the treated tress was washed with running warm water (about 40° C.) for 30 seconds.

(Drying Step)

The tress after the treatment of the step 1 was controlled by lightly squeezing such that the amount of water of the hair was 1 g, without performing the drying treatment of hair after the step 1 and the rinsing step.

(Step 2)

The tress was coated with 1 g of the hair treatment agent A (the bath ratio ((dry tress)/(hair treatment agent): 1/1) over 30 seconds and immediately thereafter, washed with running warm water (about 40° C.) for 30 seconds, followed by cool air drying with a dryer for 30 minutes to obtain a treated tress. The results of the hair dyeing property evaluation of the treated tress are shown in Table 4.

Reference Examples 1 to 3 (not Performing Step 2)

Using the aforementioned dry tress, the step 1 and the rinsing step were performed in the same manner as in Examples 1 and 2 and Comparative Example 1, the tress was then subjected to towel drying, and subsequently, the tress was dried by being blown with hot air of a dryer for 30 minutes, to obtain a treated tress. The hair dyeing property evaluation of the treated tress is shown in Table 4.

In addition, a change value of the value of a* resulting from the step 2 is also shown in Table 4.

TABLE 4

| | | Example 1 | Reference Example 1 | Example 2 | Reference Example 2 | Comparative Example 1 | Reference Example 3 |
|---|---|---|---|---|---|---|---|
| Step 1 | Hair dye composition | A | A | B | B | Comparative C | Comparative C |
| | Kind of alkaline agent | Monoethan-olamine | Monoethan-olamine | 2-amino-2-ethyl-1-propnaol | 2-amino-2-ethyl-1-propnaol | Sodium hydroxide | Sodium hydroxide |
| Drying step | Drying treatment | No | — | No | — | No | — |
| | Amount of water of hair (g per gram of tress) | 1 | — | 1 | — | 1 | — |
| Step 2 | Hair treatment agent | A | — | A | — | A | — |
| Hair dyeing property evaluation (a*) | | 3.6 | 2.7 | 4.4 | 2.5 | 1.4 | 1.9 |
| Change value of *a resulting from step 2 | | 0.9 | | 1.9 | | −0.5 | |

From comparison of Examples 1 and 2 with Comparative Example 1, in the hair dye composition (I), in the case of using the organic alkaline agent as the alkaline agent, it is exhibited that by applying the hair treatment agent (II), the value of a* is improved, and the hair is dyed to a shade of color with a strong reddish color. In particular, it is exhibited that in the case of using 2-amino-2-methyl-1-proanol as the organic alkaline agent in the hair dye composition (I), the hair dyeing properties are conspicuously improved.

Example 3 and Comparative Example 2
(Examination Regarding Drying Step after Step 1)

(Step 1 and Rinsing Step)

The aforementioned dry tress was impregnated with 5 g of the hair dye composition A for 10 minutes in a nitrogen atmosphere (the bath ratio ((dry tress)/(hair dye composition)) during impregnation: 1/5).

Subsequently, the tress was lifted up from the hair dye composition and controlled by lightly squeezing such that the bath ratio ((dry tress)/(hair dye composition)) during standing was 1/1, followed by allowing to stand for 10 minutes in an air atmosphere. After a lapse of 10 minutes, the treated tress was washed with running warm water (about 40° C.) for 30 seconds.

(Drying Step)

In Example 3, after performing the step 1 and the rinsing step, the tress was subjected to towel drying and subsequently dried by being blown with hot air of a dryer for 30 minutes. A difference from the dry mass at the time of measuring the weight of the tress at this time was taken as the amount of water of the hair.

In Comparative Example 2, after performing the step 1, the tress was subjected to towel drying and subsequently dried by being blown with hot air of a dryer for 30 minutes. The tress after dryer drying was further allowed to stand for a whole day and night or longer at a temperature of 25° C. and a relative humidity of 65%. A difference from the dry mass at the time of measuring the weight of the tress was taken as the amount of water of the hair.

(Step 2)

After performing the drying step, 1 g of the hair treatment agent A was applied to the tress over 30 seconds (the bath ratio ((dry tress)/(hair treatment agent): 1/1) and immediately thereafter, washed with running warm water (about 40° C.) for 30 seconds, followed by cool air drying with a dryer for 30 minutes to obtain a treated tress. The results of the hair dyeing property evaluation of the treated tress are shown in Table 5.

The results of Example 1 were also described in Table 5. A difference of Example 1 from Example 3 and Comparative Example 2 is that in Example 1, after the step 1 and the rinsing step, the step 2 is carried out without performing the drying treatment of the hair.

TABLE 5

| | | | Example 1 | Example 3 | Comparative Example 2 |
|---|---|---|---|---|---|
| Step 1 | Hair dye composition | | A | A | A |
| Drying step | Drying treatment | Towel drying | No | Yes | Yes |
| | | Dryer (hot air) drying time | No | 30 min | 30 min |
| | | Standing for one day | No | No | Yes |
| | | Amount of water of hair (g per gram of tress) | 1 | 0.01 | 0.005 |
| Step 2 | Hair treatment agent | | A | A | A |
| Hair dyeing property evaluation (a*) | | | 3.6 | 3.1 | 2.5 |

From comparison of Examples 1 and 3 with Comparative Example 2, it is exhibited that after performing the step 1, by subjecting the hair to the step 2 while maintaining the hair in a predetermined wet state, the value of a* is improved, and the alternation in shade of color can be made large.

Examples 4 to 6 (Examination Regarding pH of Hair Treatment Agent (II) in Step 2)

(Step 1 and Rinsing Step)

In Examples 4 to 6, the aforementioned dry tress was impregnated with 5 g of the hair dye composition A for 10 minutes in a nitrogen atmosphere (the bath ratio ((dry tress)/(hair dye composition)) during impregnation: 1/5).

Subsequently, the tress was lifted up from the hair dye composition and controlled by lightly squeezing such that the bath ratio ((dry tress)/(hair dye composition)) during standing was 1/1, followed by allowing to stand for 10 minutes in an air atmosphere. After a lapse of 10 minutes, the treated tress was washed with running warm water (about 40° C.) for 30 seconds.
(Drying Step)
The tress after the treatment of the step 1 was controlled by lightly squeezing such that the amount of water of the hair was 1 g, without performing the drying treatment of hair after the step 1 and the rinsing step.
(Step 2)
1 g of the hair treatment agent B, C, or D was applied to the tress over 30 seconds (the bath ratio ((dry tress)/(hair treatment agent)) 1/1) and immediately thereafter, washed with running warm water for 30 seconds without standing. Subsequently, the resulting tress was subjected to cool air drying with a dryer for 30 minutes to obtain a treated tress. The results of the hair dyeing property evaluation of the treated tress are shown in Table 6.

The results of Example 1 were also described in Table 6. A difference of Example 1 from Examples 4 to 6 is that in Example 1, the treatment with the hair treatment agent A is performed in the step 2.

TABLE 6

|  |  | Example | | | |
|---|---|---|---|---|---|
|  |  | 1 | 4 | 5 | 6 |
| Step 1 | Hair dye composition | A | A | A | A |
| Drying step | Drying treatment | No | No | No | No |
|  | Amount of water of hair (g per gram of tress) | 1 | 1 | 1 | 1 |
| Step 2 | Hair treatment agent | A | B | C | D |
|  | pH | 2.5 | 3.0 | 3.5 | 4.0 |
| Hair dyeing property evaluation (a*) | | 3.6 | 3.4 | 3.6 | 3.0 |

From comparison of Examples 1 and 4 to 6, it is exhibited that when the pH of the hair treatment agent (II) is 5.5 or less, the value of a* is 3.0 or more, and in particular, when the pH is in a range of less than 4.0, the effect for altering the shade of color with a reddish color is conspicuously improved.

(Examination Regarding Standing Time after Applying Hair Treatment Agent (II) in Step 2)

Examples 7 and 8

(Step 1 and Rinsing Step)
The aforementioned dry tress was impregnated with 5 g of the hair dye composition A for 10 minutes in a nitrogen atmosphere (the bath ratio ((dry tress)/(hair dye composition)) during impregnation: 1/5).
Subsequently, the tress was lifted up from the hair dye composition and controlled by lightly squeezing such that the bath ratio ((dry tress)/(hair dye composition)) during standing was 1/1, followed by allowing to stand for 10 minutes in an air atmosphere. After a lapse of 10 minutes, the treated tress was washed with running warm water (about 40° C.) for 30 seconds.
(Drying Step)
The tress after the treatment of the step 1 was controlled by lightly squeezing such that the amount of water of the hair was 1 g, without performing the drying treatment of hair after the step 1.
(Step 2)
In Example 7, 1 g of the hair treatment agent A was applied to the tress over 30 seconds (the bath ratio ((dry tress)/(hair treatment agent): 1/1), allowed to stand for 1 minute, and then washed with running warm water (about 40° C.) for 30 seconds. Subsequently, the resulting tress was subjected to cool air drying with a dryer for 30 minutes to obtain a treated tress.

In Example 8, 1 g of the hair treatment agent A was applied to the tress over 30 seconds (the bath ratio ((dry tress)/(hair treatment agent): 1/1), allowed to stand for 3 minutes, and then washed with running warm water (about 40° C.) for 30 seconds. Subsequently, the resulting tress was subjected to cool air drying with a dryer for 30 minutes to obtain a treated tress. The results of the hair dyeing property evaluation of the treated tress are shown in Table 7.

The results of Example 1 were also described in Table 7. A difference of Example 1 from Examples 7 and 8 is that in Example 1, after performing the treatment with the hair treatment agent A in the step 2, the standing time is not provided.

TABLE 7

|  |  | Example | | |
|---|---|---|---|---|
|  |  | 1 | 7 | 8 |
| Step 1 | Hair dye composition | A | A | A |
| Drying step | Drying treatment | No | No | No |
|  | Amount of water of hair (g per gram of tress) | 1 | 1 | 1 |
| Step 2 | Hair treatment agent | A | A | A |
|  | Standing time | — | 1 min | 3 min |
| Hair dyeing property evaluation (a*) | | 3.6 | 4.2 | 4.6 |

From comparison of Examples 1 and 7 and 8, there is a tendency that after applying the hair treatment agent (II), a change of the color tone rapidly occurs, and furthermore, by providing the standing time, the value of a* is improved, and an alternation of the shade of color becomes large. According to the method of the present invention, it is exhibited that even when the standing time is short such as about 1 to 3 minutes, the hair is thoroughly dyed to a shade of color with a strong reddish color.

Reference Example 4 (Examination Regarding Step of Applying Metal-Based Oxidation Catalyst on Hair)

(Treatment Step with Metal-Based Oxidation Catalyst)
1 g of the metal solution a was applied to the aforementioned dry tress over 1 minute (the bath ratio ((dry tress)/(metal solution)) during coating: 1/1), allowed to stand for 5 minutes, and then subjected to cool air drying with a dryer for 30 minutes.
(Step 1 and Rinsing Step)
The aforementioned tress treated with the metal-based oxidation catalyst was impregnated with 5 g of the hair dye composition Comparative D for 10 minutes in a nitrogen atmosphere (the bath ratio ((dry tress)/(hair dye composition)) during impregnation: 1/5).
Subsequently, the tress was lifted up from the hair dye composition and controlled by lightly squeezing such that the bath ratio ((dry tress)/(hair dye composition)) during standing was 1/1, followed by allowing to stand for 10 minutes in an air atmosphere. After a lapse of 10 minutes, the treated tress was washed with running warm water (about 40° C.) for 30 seconds.
(Drying Step)
The tress after the treatment of the step 1 was controlled by lightly squeezing such that the amount of water of the hair was 1 g, without performing the drying treatment of hair after the step 1.

(Step 2)

1 g of the hair treatment agent A was applied to the tress over 30 seconds (the bath ratio ((dry tress)/(hair treatment agent): 1/1) and immediately thereafter, washed with running warm water for 30 seconds without standing. Subsequently, the resulting tress was subjected to cool air drying with a dryer for 30 minutes to obtain a treated tress. The results of the hair dyeing property evaluation of the treated tress are shown in Table 8.

The results of Example 1 were also described in Table 8. A difference of Example 1 from Reference Example 4 is that in Example 1, the treatment step with the metal-based oxidation catalyst is not performed before the step 1 and that the hair dye composition A is used in the step 1.

TABLE 8

| | | Example 1 | Reference Example 4 |
|---|---|---|---|
| Metal treatment | Metal solution | No | a |
| | Bath ratio ((tress)/(metal solution)) | | 1/1 |
| | Applying time | | 1 min |
| | Standing time | | 5 min |
| | Drying time | | 30 min |
| Step 1 | Hair dye composition | A | Comparative D |
| Drying step | Drying treatment | No | No |
| | Amount of water of hair (g per gram of tress) | 1 | 1 |
| Step 2 | Hair treatment agent | A | A |
| Hair dyeing property evaluation (a*) | | 3.6 | 1.5 |

From comparison of Example 1 with Reference Example 4, it is exhibited that in the case of applying the metal-based oxidation catalyst on the hair, even when after performing the step 1, the hair is subjected to the step 2 while maintaining in a predetermined wet state, an alternation of color tone is hard to quickly occur.

INDUSTRIAL APPLICABILITY

According to the method of the present invention, it is possible to alter hair dyed with a melanin precursor, which typically takes on a gray to black color, to a bright natural shade of color with a stronger reddish color in a short time. Therefore, the hair treatment time can be made very short, and excellent simplicity in practical use is revealed.

The invention claimed is:

1. A hair dyeing method, comprising the following in order:

Step 1: applying on hair a hair dye composition (I) comprising (A) a compound represented by the following general formula (1A) or a salt thereof and (B) an organic alkaline agent and having a pH of 9.0 or more and 11.0 or less:

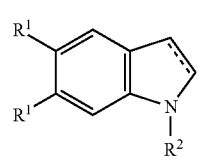

wherein a broken line represents the presence or absence of a π bond; $R^1$ represents a hydroxy group or an acetoxy group; and $R^2$ represents a hydrogen atom, an acetyl group, a methyl group, or an ethyl group; and Step 2: applying on the hair a hair treatment agent (II) comprising (C) an organic acid or a salt thereof and having a pH of 5.5 or less, wherein after performing the step 1, the hair is subjected to the step 2 while maintaining in a wet state in which an amount of water per gram of the hair is 0.008 g or more.

2. The hair dyeing method according to claim 1, wherein a content of the component (A) in the hair dye composition (I) is 0.05% by mass or more and 5% by mass or less.

3. The hair dyeing method according to claim 1, wherein the component (B) is one or more selected from the group consisting of ammonia, an alkanolamine, an alkylamine, and an aralkylamine.

4. The hair dyeing method according to claim 1, wherein the component (C) is one or more selected from the group consisting of an aliphatic carboxylic acid having 8 or less carbon atoms, an aromatic sulfonic acid having 10 or less carbon atoms, and a salt thereof.

5. The hair dyeing method according to claim 1, further comprising rinsing the hair between the step 1 and the step 2.

6. A hair dyeing kit, comprising:
a hair dye composition (I) comprising (A) a compound represented by the following general formula (1A) or a salt thereof and (B) an organic alkaline agent and having a pH of 9.0 or more and 11.0 or less; and
a hair treatment agent (II) comprising (C) an organic acid or a salt thereof and having a pH of 5.5 or less:

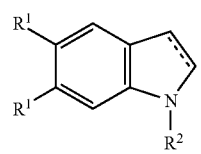

wherein a broken line represents the presence or absence of a π bond; $R^1$ represents a hydroxy group or an acetoxy group; and $R^2$ represents a hydrogen atom, an acetyl group, a methyl group, or an ethyl group.

* * * * *